US011930829B2

(12) United States Patent
Pein (10) Patent No.: US 11,930,829 B2
(45) Date of Patent: Mar. 19, 2024

(54) DEVICE AND ARRANGEMENT FOR OPTICALLY INSPECTING ARTICLES IN THE FISH AND MEAT PROCESSING INDUSTRY

(71) Applicant: Nordischer Maschinenbau Rud. Baader GmbH + Co. KG, Lübeck (DE)

(72) Inventor: Roland Pein, Herrnburg (DE)

(73) Assignee: Nordischer Maschinenbau Rud. Baader GmbH & Co. KG, Lübeck (DE)

( * ) Notice: Subject to any disclaimer, the term of this patent is extended or adjusted under 35 U.S.C. 154(b) by 851 days.

(21) Appl. No.: 16/963,807

(22) PCT Filed: Jan. 23, 2019

(86) PCT No.: PCT/EP2019/051647
§ 371 (c)(1),
(2) Date: Jul. 21, 2020

(87) PCT Pub. No.: WO2019/145367
PCT Pub. Date: Aug. 1, 2019

(65) Prior Publication Data
US 2020/0359637 A1   Nov. 19, 2020

(30) Foreign Application Priority Data

Jan. 26, 2018   (DE) .......................... 102018101835.5

(51) Int. Cl.
*A22B 5/00* (2006.01)
*G01N 21/15* (2006.01)
*G01N 33/12* (2006.01)

(52) U.S. Cl.
CPC ............. *A22B 5/007* (2013.01); *G01N 21/15* (2013.01); *G01N 33/12* (2013.01); *G01N 2021/157* (2013.01)

(58) Field of Classification Search
CPC ........ A22B 5/007; G01N 21/15; G01N 33/12; G01N 2021/157
See application file for complete search history.

(56) References Cited

U.S. PATENT DOCUMENTS 6,649,412 B1 * 11/2003 Borggaard ............. A22C 25/04
436/60
8,092,283 B2 * 1/2012 Hansen ................ A22C 25/142
452/121
(Continued)

FOREIGN PATENT DOCUMENTS

DE   202006019722 U1   4/2008
DE   102007023480 A1   11/2008
(Continued)

OTHER PUBLICATIONS

Kroma A/s. "Visiomaster—The good result is now visible", Internet, May 22, 2008 (May 22, 2008), Retrieved from the Internet: http://www.odinmakine.com.tr/fileadmin/user_upload/BrosurMakinelerWebSitesi/8-SuurunleriislemeMakineleri/2-KromaAS/Katalog/12-VisionMaster. pdf [retrieved on Jan. 13, 2019] XP055334652.

(Continued)

Primary Examiner — Solomon G Bezuayehu
(74) Attorney, Agent, or Firm — Dinsmore & Shohl LLP (57) ABSTRACT

An apparatus, designed and configured for optically inspecting articles of the fish and meat processing industry, includes at least one imaging system which is arranged so as to be encapsulated on all sides in a housing and is configured for optically scanning the articles. The housing has a transparent viewing window and a protective element, forming a light- (Continued)

transmissive channel, and is releasably arranged on the outside of the housing to protect the viewing window from contamination. In addition, an arrangement for processing and inspecting the opened abdominal cavity of gutted fish, includes a conveying device configured for conveying the fish along a processing line in the longitudinal direction, which is characterised in that the arrangement comprises at least one apparatus configured for optically inspecting the abdominal cavity.

12 Claims, 5 Drawing Sheets

(56) References Cited

U.S. PATENT DOCUMENTS

| | | | |
|---|---|---|---|
| 8,253,791 B2 | 8/2012 | Gruber-Nadlinger et al. | |
| 10,371,597 B2* | 8/2019 | Zhang | G01N 21/9515 |
| 10,412,275 B2* | 9/2019 | Shaw | H04N 7/183 |
| 10,531,668 B2 | 1/2020 | Steffens et al. | |
| 2006/0009257 A1* | 1/2006 | Ku | G01N 33/4972 |
| | | | 455/556.1 |
| 2009/0033743 A1* | 2/2009 | Gruber-Nadlinger | G03B 17/02 |
| | | | 348/86 |
| 2009/0087033 A1* | 4/2009 | Chao | G06V 40/10 |
| | | | 382/110 |
| 2011/0273558 A1* | 11/2011 | Subbiah | G01N 21/3563 |
| | | | 348/E7.085 |
| 2012/0287285 A1* | 11/2012 | Jensen | F26B 25/009 |
| | | | 348/E5.09 |
| 2013/0070233 A1 | 3/2013 | Chang et al. | |
| 2017/0142302 A1* | 5/2017 | Shaw | B02C 17/1805 |
| 2017/0356824 A1* | 12/2017 | Zhang | G01M 13/021 |
| 2018/0125345 A1* | 5/2018 | Rebella | A61B 1/015 |
| 2019/0116810 A1* | 4/2019 | Steffens | G05B 19/416 |

FOREIGN PATENT DOCUMENTS

| | | |
|---|---|---|
| DE | 102015204554 B4 | 9/2016 |
| WO | 9316351 A1 | 8/1993 |
| WO | 2007090724 A1 | 8/2007 |
| WO | 2017186275 A1 | 11/2017 |

OTHER PUBLICATIONS

International Search Report dated Mar. 22, 2019; International Application No. PCT/EP2019/051647.

* cited by examiner

DEVICE AND ARRANGEMENT FOR OPTICALLY INSPECTING ARTICLES IN THE FISH AND MEAT PROCESSING INDUSTRY

CROSS-REFERENCE TO RELATED APPLICATIONS

This application is the U.S. national stage of PCT/EP2019/051647 filed Jan. 23, 2019, which claims priority of German Patent Application 102018101835.5 filed Jan. 26, 2018; each of which is hereby incorporated by reference in its entirety.

FIELD OF INVENTION

The present invention concerns an apparatus designed and configured for optically inspecting articles in the fish and meat processing industry. In addition, the invention relates to an arrangement for processing and inspecting the opened abdominal cavity of gutted fish, said arrangement comprising a conveying device configured for conveying the fish along a processing line in the longitudinal direction.

BACKGROUND OF THE INVENTION

Such apparatuses are used in the industrial processing of fish and meat products. The handling and processing of such articles is carried out largely using automatically controlled tools. The processing steps are monitored optically for monitoring and control purposes. For this purpose, the articles to be processed or the articles processed are scanned using an optical imaging system and the image data thus obtained is evaluated semi- or fully automatically.

The arrangement referred to hereinbefore is used in industrial fish processing. In this case, the fish are fed to an automatic slaughtering device which, among other things, opens the abdominal cavity of the fish and automatically removes the guts therefrom due to the intervention of appropriate tools. To check the result of this gutting process, the abdominal cavity of the fish is then optically scanned and, using suitable image processing algorithms, appropriate tests are carried out based on the image data obtained.

With the known apparatuses and arrangements, the imaging systems are exposed to contaminants which may arise during the processing procedure. Within a relatively short time, blood and tissue residues, various dirt particles and/or drops of liquid, for example, settle on the lenses of the imaging systems or in their field of view. As the degree of contamination increases, the unobstructed view of the imaging system onto the areas of the articles to be scanned is so adversely affected that the result can range from incorrect image evaluations to total failure of the optical inspection. In this case, the entire production process must be stopped and the relevant components must first be cleaned which means that undesirable downtimes and production interruptions occur.

SUMMARY OF THE INVENTION

It is therefore the object of the present invention to propose an apparatus of the type referred to hereinbefore which guarantees the most reliable optical inspection of the said articles and at the same time can be cleaned as easily, conveniently and quickly as possible. The object is additionally to propose an arrangement of the type referred to hereinbefore which enables a reliable optical inspection of the opened abdominal cavity of gutted fish and at the same time permits fast and hygienic cleaning of the components relevant for the optical inspection.

The object is achieved by the apparatus referred to hereinbefore, the apparatus comprising at least one imaging system which is arranged so as to be encapsulated on all sides in a housing and is configured for optically scanning the articles, the housing having a transparent viewing window and a protective element, forming a light-transmissive channel, which is releasably arranged on the outside of the housing to protect the viewing window from contamination. In this way, the imaging system is protected on the one hand from direct exposure to contamination by the transparent viewing window. On the other hand, the protective element shields the viewing window, particularly in the detection zone of the imaging system, and keeps the viewing or detection zone of the imaging system free of contamination as far as possible or greatly reduces the adhesion of contamination to the viewing window.

Another advantage is that the protective element is releasably arranged on the viewing window on the outside of the housing. For cleaning purposes, the protective element can therefore be quickly and easily removed from the viewing window and the viewing window and the protective element can be cleaned. Since the protective element is removable, it can be cleaned and—if necessary—disinfected separately.

The arrangement of the imaging system which is encapsulated on all sides in the housing substantially simplifies cleaning of the apparatus according to the invention since the imaging system is arranged so as to be protected, in particular splash-proof and jet-proof, and therefore no separate consideration must be given to sensitive components of the imaging system during the cleaning process.

From a hygiene point of view, which is regularly subject to particularly high requirements in the fish and meat processing industry, the structure of the apparatus according to the invention, which is kept as simple as possible, has a particularly positive effect. In this way, any accumulation of contaminants in inaccessible areas, which is otherwise possible, is largely excluded. The housing and the viewing window comprise surfaces that are as flat or smooth as possible which are particularly easy and convenient to clean and essentially have no protruding and/or undercut outer geometry that would encourage adhesion of contaminants and complicate the cleaning process overall.

An advantageous development of the invention is characterised in that the protective element is arranged on the viewing window and encloses at least one detection zone of the imaging system while maintaining an unobstructed view of the articles. Advantageously, the protective element thus does not restrict the field of view of the imaging system or only restricts it insignificantly. At the same time, the detection zone of the imaging system is effectively shielded against the entry of contaminants arising during the processing procedure. This reliably prevents such contaminants from striking the viewing window in the relevant detection zone. The protective element preferably encloses the detection zone of the imaging system on all sides. Further preferably, the protective element is arranged centred in the middle with regard to the imaging system such that the shielding and protective effect of the protective element is present in the same form for each partial region of the detection zone. The protective element is thus preferably arranged in such a manner that an imaginary central axis of the protective element coincides with the visual axis of the imaging system.

According to a preferred development of the invention, the protective element has a protective element base with a central light transmittance recess and holding means are present on the housing side which are configured in each case to arrange the protective element base releasably on the viewing window. The protective element base is designed as a supporting and contact element and is configured to rest on the viewing window. The protective element base is preferably designed such that it protrudes laterally beyond the channel wall of the light-transmissive channel. The protective element base is thus designed as a standing or contact surface extension by means of which the protective element base can be arranged flat on the viewing window.

Preferably, one contact surface of the protective element base is designed flat and, in the arranged state, lies flush with the viewing window on the outside of the housing. This has the advantage of effectively preventing undesirable ingress of liquids and/or dirt between the contact surface and the viewing window.

Preferably, holding means are arranged on the housing side which are configured for releasable arrangement of the protective element base on the viewing window. Further preferably, the holding means are arranged on the inside of the housing. The holding means are designed in particular as holding magnets or comprise such. The protective element base advantageously also has holding magnets and/or is made of a magnetic or magnetisable material.

According to an expedient embodiment of the invention, the protective element base is configured to merge seamlessly into the channel wall forming the light-transmissive channel. Advantageously, the channel wall and the protective element base thus form a continuously closed enveloping surface. In this way, the region of the viewing window to be protected in the detection zone of the imaging sensor is optimally shielded against contaminants. Further preferably, the channel wall and the protective element base are formed integrally.

An advantageous development of the invention provides for the channel wall of the protective element to be shaped as a hollow cylinder with a circular, elliptical, rectangular or polygonal cross-sectional area. The shielding effect can be optimally adapted to the relevant application by selecting the geometry of the cross-sectional area. For example, when processing articles of the fish and meat processing industry, it is thus possible to keep certain contaminants, which hit the apparatus according to the invention from a preferred direction, away from the impact surfaces formed by the channel wall. The impact surfaces formed by the channel walls can be adapted accordingly depending on the intended use and the main direction from which a build-up of contaminants is to be expected as a result.

According to a further advantageous embodiment, the channel wall of the protective element is designed as a hollow truncated cone or hollow truncated pyramid. In other words, the protective element or the channel wall of the protective element is funnel-shaped. The side with smaller cross-section is preferably directed towards the viewing window such that the channel cross-section widens in the direction of the articles to be inspected. This means that with the size of the protective element as small as possible, the influence of the protective element itself on the optical beam path is reduced to a minimum such that the articles in the detection zone of the imaging system can be detected unhindered. In this way, the channel walls are optimally adapted to the widening of the optical beam path that occurs with increasing distance from the imaging system.

The object is also achieved by the arrangement referred to hereinbefore which is characterised in that said arrangement includes at least one apparatus with the previously described features that is configured for optically inspecting the abdominal cavity. The advantages emerging from the apparatus according to the invention and presented above apply equally to the arrangement according to the invention. To avoid repetition, reference is therefore made thereto.

An advantageous development is characterised in that the conveying device is configured to convey the fish lying with the opened abdominal cavity pointing upwards, the at least one apparatus being arranged above the processing line with the viewing window pointing towards the processing line. This has the advantage that contaminants arising during the processing procedure are deflected downwards following the force of gravity and the proportion of contaminants penetrating the area of the apparatus according to the invention is considerably reduced as a result.

According to a further embodiment, at least one of the protective elements is arranged in such a manner that the light-transmissive channel is oriented at least substantially perpendicular to the longitudinal direction. The solid and liquid constituents arising during processing of the fish are distributed randomly in all spatial directions. Upwardly directed moving components of the constituents are "braked" by the effect of the force of gravity such that the constituents move substantially on more or less curved tracks. The probability that constituents will move against the force of gravity in a path directed substantially perpendicular to the ground is therefore much lower compared to other path directions. By orienting the light-transmissive channel perpendicular or substantially perpendicular to the longitudinal direction, the channel is oriented such that the unobstructed opening of the channel leg points in the direction from which the lowest proportion of the said constituents that might lead to possible contamination of the viewing window is to be expected.

The arrangement according to the invention preferably comprises at least one illumination device configured for illuminating the abdominal cavity of the fish, the illumination device being arranged on the viewing window on the inside of the housing space apart laterally from the at least one imaging system.

According to an advantageous development of the invention, it is provided that the at least one illumination device is designed as a surface-emitting diode, the radiating surface of which is arranged sloping with respect to the viewing window. This ensures the most uniform illumination of the abdominal cavity. In addition, the illuminance is increased by the superposition of a plurality of light sources.

An expedient embodiment is characterised in that the radiating surface slopes such that in each case the main light emission direction is oriented sloping towards a viewing line between imaging system and abdominal cavity. Any shadow formation arising due to the protective element is excluded in this manner by illumination from both sides thus achieved illumination of the abdominal cavity which is as homogeneous as possible.

Preferably, the at least one illumination device is arranged on the viewing window, forming an air gap. This ensures optimum cooling of the illumination devices and compliance with the maximum permissible operating temperature. In addition, the illumination devices are ventilated in this way, which counteracts any condensation that might otherwise form between the radiating surfaces of the illumination devices and the viewing window.

BRIEF DESCRIPTION OF THE DRAWINGS

Further preferred and/or expedient features and embodiments of the invention emerge from the dependent claims and the description. Especially preferred embodiments are explained in greater detail with reference to the attached drawing. The drawing shows:

DETAILED DESCRIPTION OF THE PREFERRED EMBODIMENTS

Figure 1:
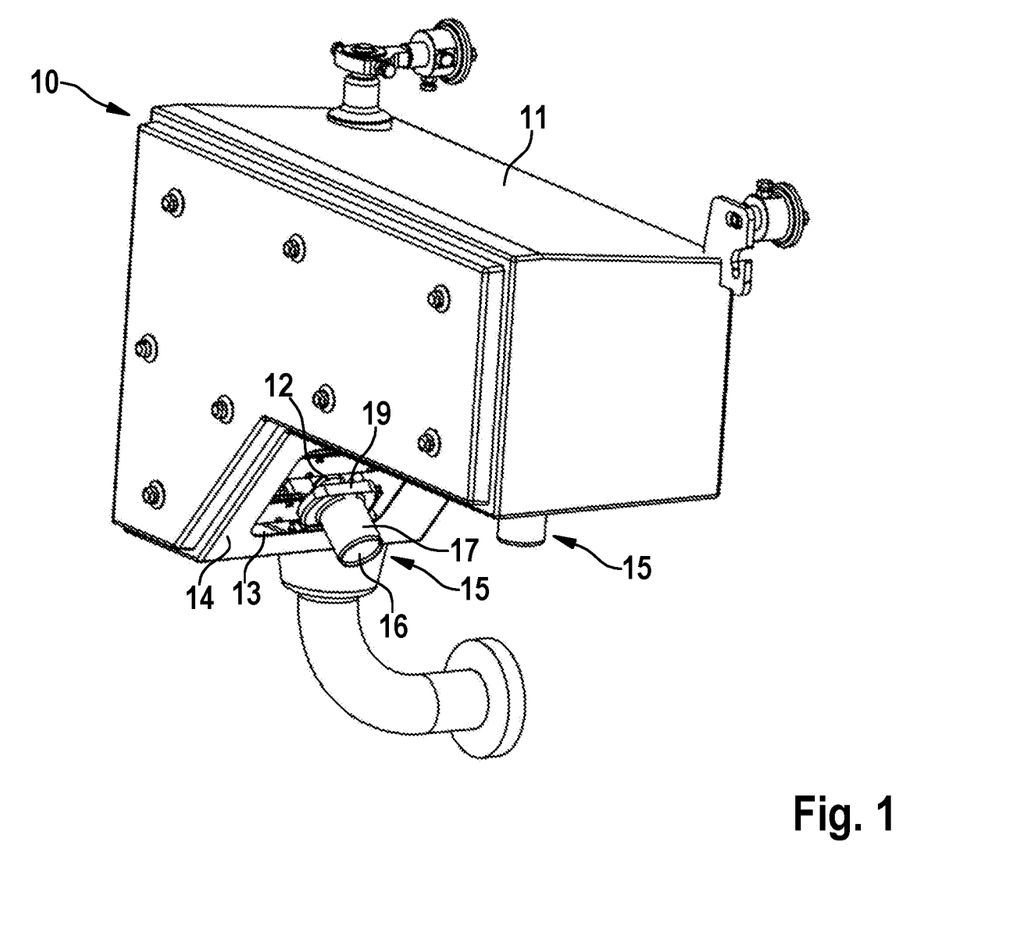
FIG. 1 is a perspective view of the apparatus according to the invention.

FIG. 1 shows a perspective view of the apparatus 10 according to the invention. The apparatus 10 is designed and configured for optically inspecting articles in the fish and meat processing industry. For example, when processing fish, it is thus necessary to check the processing result after processing in order to initiate further post-processing steps if necessary. The apparatus 10 shown comprises a housing 11 in which an imaging system 12, configured for optically scanning the articles, is arranged so as to be encapsulated on all sides. In FIG. 1, only one imaging system 12 is visibly shown, while a second imaging system, preferably arranged in the housing 11, is covered by said housing 11 in the illustration of FIG. 1. The number of imaging systems 12 arranged in the housing 11 is basically arbitrary, but depends on which regions of the articles of the fish and meat processing industry are to be optically inspected. The housing 11 also has a transparent viewing window 13 which is preferably arranged on the article side of the housing 11 or forms a light-transmissive recess on this housing side 14.

On the outside of the housing, a protective element 15 is releasably arranged on the viewing window 13. The protective element 15 forms a light-transmissive channel 16. Starting from the respective imaging system 12, the protective element 15 with its light-transmissive channel 16 forms an unobstructed visual axis onto an inspection area which is optically scanned by the respective imaging system for inspecting the articles.

The protective element 15 is used to protect the viewing window 13 from contamination, for example by blood and/or tissue residues, and from liquid being deposited on the viewing window 13. The light-transmissive channel 16 of the protective element 15 is preferably designed to be lens-free. In other words, in particular there are no refractive optical elements, such as lenses or optical filters, arranged inside the light-transmissive channel 16. Thus the light-transmissive channel 16 is advantageously formed exclusively by a channel wall 17, which on the one hand serves as a shielding element for the viewing window 13 and shields it from the said contaminants along the visual axis, and on the other hand advantageously fulfils the function of a lens hood. In addition to the protective function from contaminants of the viewing window 13, this effectively shields and attenuates the incidence of light on the at least one imaging system 12 by light beams which do no run substantially parallel to the visual axis of the imaging system 12.

Figure 2:
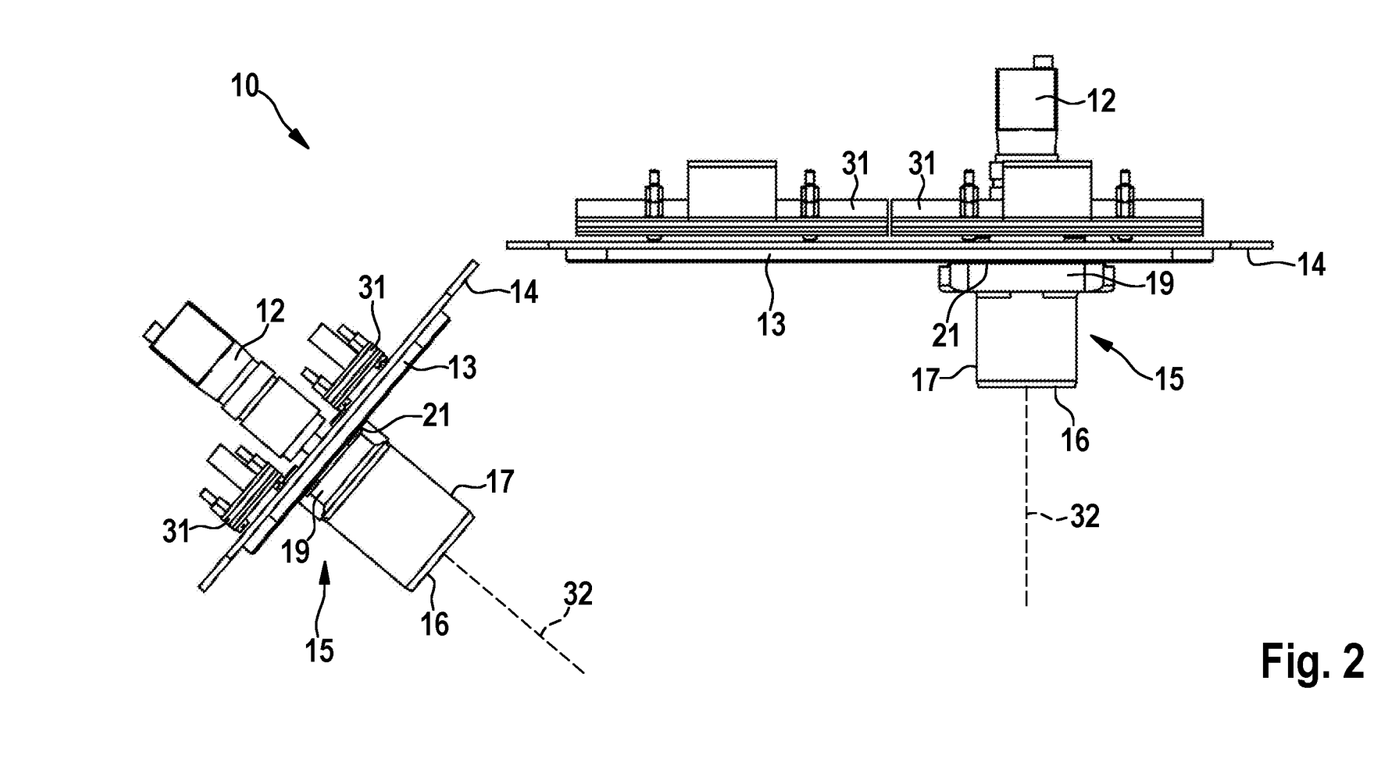
FIG. 2 is a lateral view of the apparatus according to the invention without housing.

FIG. 2 shows a lateral view of the apparatus according to the invention, only the housing side 14 being shown for reasons of better clarity. The apparatus according to the invention shown by way of example in FIG. 2 comprises two of the imaging systems 12, which are arranged in each case sloping towards each other such that in each case they inspect the articles of the fish and meat processing industry from different angles. Each of the imaging systems 12 is associated in each case with one of the transparent viewing windows 13 which, as shown in FIG. 2, is designed in two parts according to an advantageous embodiment of the invention. Each of the imaging systems 12 is associated in each case with one of the protective elements 15 which in each case are releasably arranged on the respective viewing window 13 on the outside of the housing.

The protective element 15 is advantageously arranged on the viewing window 13 in such a manner that at least one detection zone of the imaging system 12 is enclosed while maintaining an unobstructed view of the articles. The detection zone of the imaging system 12 denotes the region within which the imaging system 12 is able to optically scan the articles. Starting from the imaging system 12, a partial area of the viewing window 13 is thus to be considered as belonging to the detection zone. The protective element 15 is then arranged around this partial area such that on the one hand said area is enclosed on all sides by the protective element 15, but on the other hand, with the exception of the shielding function against stray light previously described, it does not result in any restriction of the field of view on the part of the imaging system. The protective element 15 is preferably arranged centred in the middle with regard to the imaging system 12 on the viewing window 13.

Figure 4:
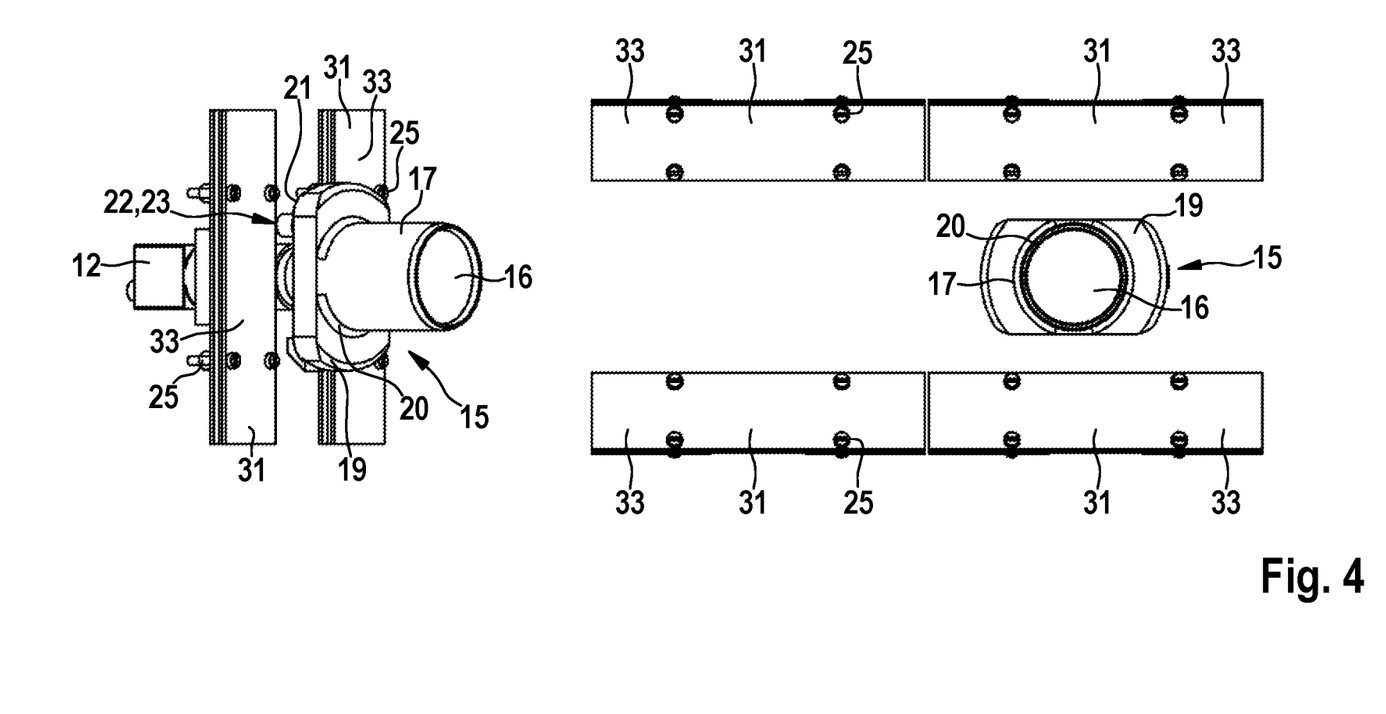
FIG. 4 is a schematic illustration of the apparatus according to the invention in top view, looking onto the viewing window from outside and FIG. 5 a perspective view of the arrangement according to the invention.

The protective element 15 has a protective element base 19. As can be seen in FIG. 4, the protective element base 19 comprises a central light transmittance recess 20. The light transmittance recess 20 is preferably arranged flush with the light-transmissive channel 16. The protective element base 19 preferably protrudes at least laterally beyond the channel wall 17 of the protective element 15, such that the protective element base 19 forms a contact surface 21 by means of which the protective element base 19 can be arranged flat on the viewing window 13.

Further preferably, the contact surface 21 is designed flat and, in the arranged state, lies flush with the viewing window 13 on the outside of the housing. In this manner, undesirable ingress of liquids and/or dirt between the contact surface 21 and the viewing window 13 is precluded.

Holding means 22, which are configured to arrange the protective element base 19 releasably on the viewing window 13, are present on the housing side. As shown in the perspective interior view of the apparatus according to the invention with the housing hidden in FIG. 3, the holding means 22 are preferably arranged on the inside of the housing. Further preferably, the holding means 22 are designed as holding magnets 23 or in each case comprise these holding magnets 23.

Figure 3:
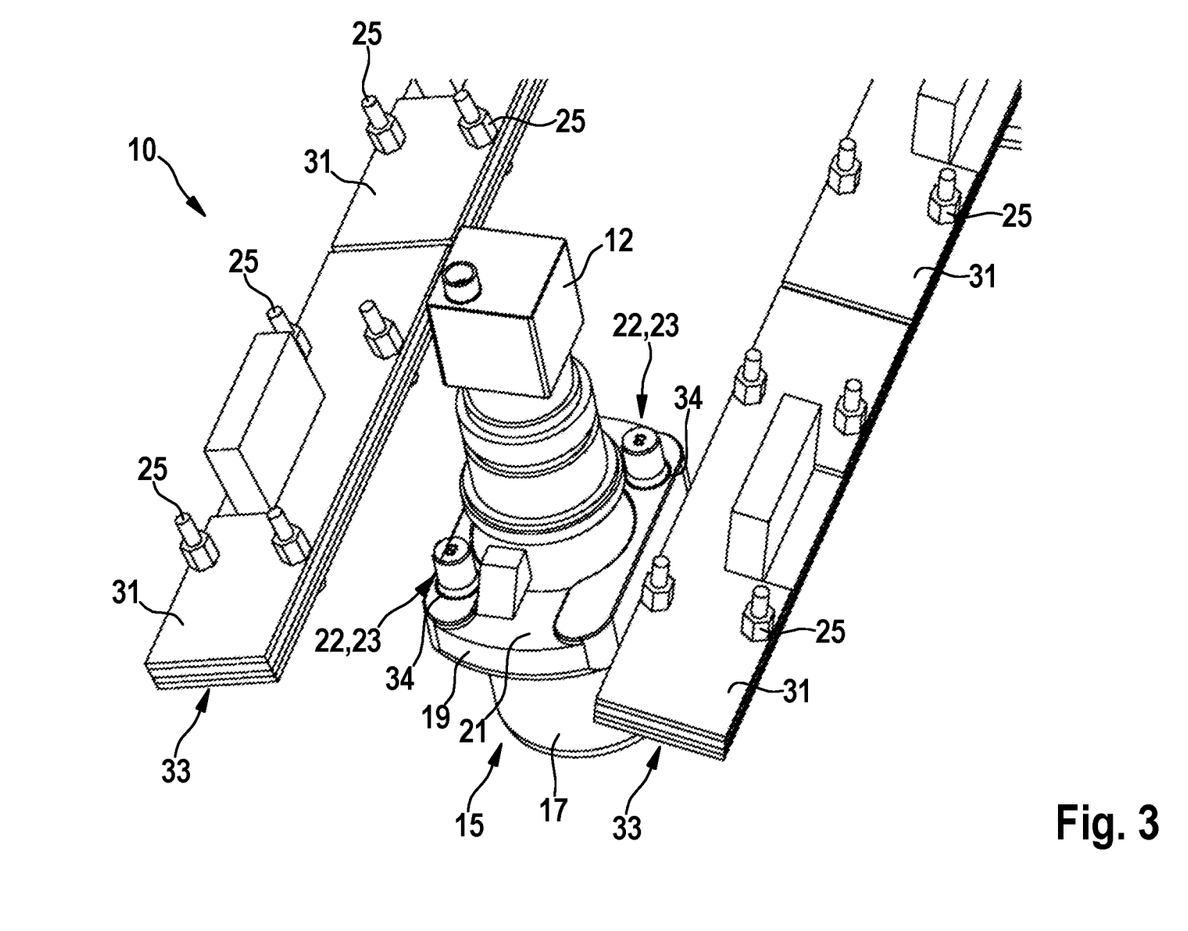
FIG. 3 is a perspective interior view of the apparatus according to the invention with the housing hidden

The protective element base 19 comprises at least in part, i.e. at least in some partial areas, a magnetic and/or magnetisable material. The protective element base 19, for example, is made partly or completely of a ferromagnetic material. Alternatively, the protective element base 19 comprises magnets 34 and/or ferromagnetic partial areas embedded in the contact surface 21. In any case, the polarities of the holding magnets 23 and those of the protective element base 19 are oriented in such a manner that they attract each other and thus the entire protective element 15 is held in place independently on the viewing window 13. A further advantage is that the protective element 15 can be positioned in a clearly centred arrangement due to the opposite polarities.

A particular advantage in the previously described embodiment of the holding means 22 and the protective element base 19 is the particular ease of handling the apparatus according to the invention. Thus, the protective element 15 can be arranged on the viewing window 13 with a simple movement of the hand, without complicated installation work. For cleaning and maintenance purposes, the protective element 15 according to the invention can be detached from the viewing window 13 in the same manner with a simple movement of the hand. This has a particular impact on the high hygiene requirements that are regularly present in the fish and meat processing industry. After removing the protective element 15 from the viewing window 13, the viewing window 13 can be cleaned with particular ease as a flat component and there is no risk of contaminants remaining in hard-to-reach places due to complex outer geometries. In addition, the protective element 15 once removed can be cleaned and disinfected separately.

Advantageously, the protective element base 19 is configured such that it merges gap-free into a channel wall 17 forming the light-transmissive channel 16. In other words, the channel wall 17 and the protective element base 19 form a continuously closed envelope which shield the light-transmissive channel 16 and the light transmittance recess 20. Further preferably, the channel wall 17 and the protective element base 19 are formed integrally.

The channel wall 17 of the protective element 15 is preferably shaped as a hollow cylinder. As shown in the drawing, this hollow-cylinder-shaped embodiment of the channel wall 17 preferably has a circular cross-sectional area. Alternatively, the cross-sectional area is configured, for example, to be elliptical, rectangular or any other polygonal shape. Particularly in the case of a non-circular cross-sectional area, it is possible to achieve an increased or reduced shielding effect against dirt and ingress of liquids by choosing a corresponding geometry of the cross-sectional area. For example, when processing articles of the fish and meat processing industry, it is thus possible to keep certain contaminants, which hit the apparatus according to the invention from a preferred orientation, away from impact surfaces formed by the channel wall 17.

When using an elliptical cross-sectional area, the channel wall 17 of the protective element 15, for example, can be oriented in such a manner that the main axis of the elliptical cross-sectional area is perpendicular or at least substantially perpendicular to the preferred orientation from which the largest proportion of dirt/contamination arising during processing of the articles is to be expected.

In addition, the present invention is illustrated schematically in FIG. 4 and show the apparatus according to the invention in top view, looking onto the viewing window 13. The viewing window 13 is not shown in FIG. 4 and neither is the housing 11.

Figure 5:
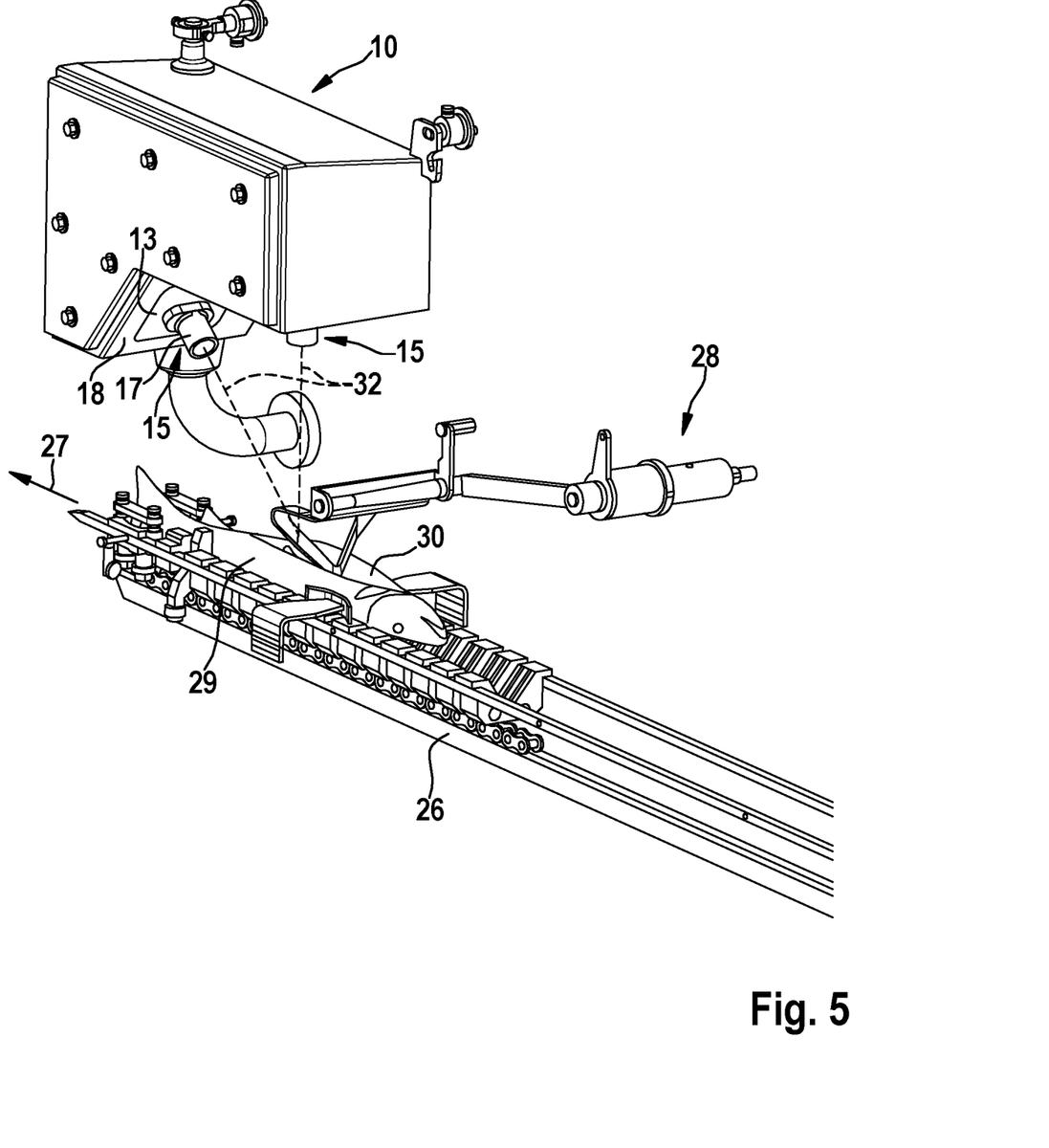

FIG. 5 shows a perspective view of the arrangement according to the invention for processing and inspecting the opened abdominal cavity 30 of gutted fish 29. The arrangement according to the invention comprises a conveying device 26 which is configured for conveying the fish along a processing line 28 in the longitudinal direction 27. For the sake of clarity, the processing line 28 is shown simplified in the form of only one tool for holding open the abdominal cavity 30 of the fish.

The arrangement further comprises at least one apparatus 10 according to the invention which has been described in detail above and is configured for optically inspecting the abdominal cavity 30. As can be seen in FIG. 5, the apparatus 10 according to the invention is arranged above the conveying device 26 and the processing line 28. The fish 29 transported by means of the conveying device 26 are supported on the conveying device 26 on the dorsal side such that their abdominal cavity 30 is pointing upwards. This has the advantage that liquid atomised spray and/or tissue parts of the fish 29 arising during processing of said fish 29, which can lead to contamination of the viewing window 13, are deflected downwards due to gravity.

Those liquid or tissue parts which get into the vicinity of the apparatus 10 according to the invention are, as previously described, largely prevented from striking the viewing window 13 in the region of the respective imaging system 12 by the protective element 15 according to the invention. It is therefore especially advantageous that the conveying device 26 is configured to convey the fish 29 lying with the opened abdominal cavity 30 pointing upwards and to arrange the at least one apparatus 10 above the processing line 28 with the viewing window 13 pointing towards said processing line 28.

Preferably, at least one of the protective elements 15 is arranged in such a manner that the light-transmissive channel 16 is oriented at least substantially perpendicular to the longitudinal direction 27. As shown in FIG. 5, one of the protective elements 15, which is upstream with respect to the longitudinal direction 27, is arranged exactly perpendicular in relation to the longitudinal direction 27. The further downstream protective element 15 is arranged sloping with respect to the longitudinal direction 27, i.e. it deviates slightly from the vertical orientation.

As shown in FIGS. 2, 3 and 4, the arrangement according to the invention comprises at least one illumination device 31 configured for illuminating the abdominal cavity 30 of the fish 29. Each of the illumination devices 31 is preferably arranged on the viewing window 13 on the inside of the housing and in each case is spaced apart laterally from the at least one imaging system 12. As shown in FIG. 4, for example, four of the illumination devices 31 are arranged around the protective element 15 spaced apart laterally. Two each of the illumination devices 31 are arranged laterally next to the imaging system 12 shown on the left in FIG. 4.

Advantageously, the at least one illumination device 31 is designed as a surface-emitting diode. For this purpose, the illumination device 31 comprises LED arrays, for example. Further preferably, its radiating surface 33 is arranged sloping with respect to the viewing window 15, in particular the radiating surface 33 slopes such that in each case the main light emission direction is oriented sloping towards one of the viewing lines 32 between the respective imaging system 12 and the abdominal cavity 30. On the one hand, this increases the illuminance by superposing the light outputs of the illumination devices 31. On the other hand, the illumination devices 31 arranged on both sides of the protective element 15 ensure uniform illumination of the abdominal cavity 30 and prevent possible shadows due to the protective element 15 itself.

The illumination devices 31 shown are each arranged on the viewing window 15, forming an air gap. This ventilation of the illumination devices 31 has a positive effect on the dissipation of waste heat arising and at the same time has the advantage that possible formation of condensation between the viewing window 13 and the radiating surface 33 is prevented.

The illumination devices 31 are preferably releasably arranged on the viewing window 13 or on the housing side 14 by means of screw connections 25.

The invention claimed is:

1. An apparatus designed and configured for optically inspecting articles in the fish and meat processing industry, comprising:
   at least one imaging system which is arranged so as to be encapsulated on all sides in a housing and is configured for optically scanning the articles;
   the housing having a transparent viewing window; and
   a protective element, forming a light-transmissive channel releasably arranged on an outside of the housing to protect the viewing window from contamination, wherein:
      the protective element is arranged on the viewing window and encloses at least one detection zone of the imaging system while maintaining an unobstructed view of the articles,
      the protective element comprises a protective element base with a central light transmittance recess and holding means, which are configured in each case to arrange the protective element base releasably on the viewing window, are present on the housing side, and
      the holding means are arranged on an inside of the housing and are designed as holding magnets and the protective element base comprises at least in part a magnetic and/or magnetisable material.

2. The apparatus according to claim 1, wherein the protective element base is configured to merge gap-free into a channel wall forming the light-transmissive channel.

3. The apparatus according to claim 2, wherein the channel wall and the protective element base are formed integrally.

4. The apparatus according to claim 2, wherein the channel wall of the protective element is shaped as a hollow cylinder with a circular, elliptical, rectangular or polygonal cross-sectional area.

5. The apparatus according to claim 2, wherein the channel wall of the protective element is designed as a hollow truncated cone or hollow truncated pyramid.

6. An arrangement for processing and inspecting an opened abdominal cavity of gutted fish, comprising:
   a conveying device configured for conveying the fish along a processing line in the longitudinal direction,
   at least one apparatus configured for optically inspecting the abdominal cavity according to claim 1.

7. The arrangement according to claim 6, wherein the conveying device is configured to convey the fish lying with the opened abdominal cavity pointing upwards, wherein the at least one apparatus is arranged above the processing line with the viewing window pointing towards said processing line.

8. The arrangement according to claim 7, wherein the protective element is arranged in such a manner that the light-transmissive channel is oriented at least substantially perpendicular to the longitudinal direction.

9. The arrangement according to claim 6, further comprising at least one illumination device configured for illuminating the abdominal cavity of the fish, wherein the at least one illumination device is arranged on the viewing window on an inside of the housing spaced apart laterally from the at least one imaging system.

10. The arrangement according to claim 9, wherein the at least one illumination device is designed as a surface-emitting diode, a radiating surface of which is arranged sloping with respect to the viewing window.

11. The arrangement according to claim 10, wherein the radiating surface is inclined such that in each case a main light emission direction is oriented sloping towards a viewing line between the imaging system and the abdominal cavity.

12. The arrangement according to claim 9, wherein the at least one illumination device is arranged on the viewing window, forming an air gap.

* * * * *